United States Patent
Kojima et al.

(10) Patent No.: US 8,846,011 B2
(45) Date of Patent: Sep. 30, 2014

(54) CURABLE RESIN COMPOSITION FOR COVERING A FINGERNAIL OR ARTIFICIAL FINGERNAIL

(75) Inventors: Kazuhiro Kojima, Saint Ouen l'Aumone (FR); Khoi-Nguyen Ha, Saint Ouen l'Aumone (FR); Leroy Anthony, Saint Ouen l'Aumone (FR)

(73) Assignee: Threebond Fine Chemical Co., Ltd., Sagamihara-shi (JP)

( * ) Notice: Subject to any disclaimer, the term of this patent is extended or adjusted under 35 U.S.C. 154(b) by 0 days.

(21) Appl. No.: 13/514,818

(22) PCT Filed: Dec. 7, 2010

(86) PCT No.: PCT/JP2010/071862
§ 371 (c)(1),
(2), (4) Date: Jul. 12, 2012

(87) PCT Pub. No.: WO2011/071029
PCT Pub. Date: Jun. 16, 2011

(65) Prior Publication Data
US 2012/0276028 A1    Nov. 1, 2012

(30) Foreign Application Priority Data

Dec. 8, 2009 (JP) .................. 2009-278268

(51) Int. Cl.
*A61K 8/00* (2006.01)
*A61Q 3/02* (2006.01)
*A61K 8/55* (2006.01)
*A61K 8/81* (2006.01)
*A61K 8/37* (2006.01)
*A61K 8/92* (2006.01)
*A61K 8/86* (2006.01)

(52) U.S. Cl.
CPC ............... *A61Q 3/02* (2013.01); *A61K 2800/81* (2013.01); *A61K 8/55* (2013.01); *A61K 8/8152* (2013.01); *A61K 8/37* (2013.01); *A61K 8/922* (2013.01); *A61K 8/86* (2013.01)
USPC ............................................................ 424/61

(58) Field of Classification Search
USPC ........................................................... 424/61
See application file for complete search history.

(56) References Cited

U.S. PATENT DOCUMENTS 4,250,007 A * 2/1981 Yasuno et al. ................. 522/142
4,526,920 A * 7/1985 Sakashita et al. ............... 522/78

FOREIGN PATENT DOCUMENTS

| EP | 1866357 B1 * | 2/2012 |
| JP | 04-103513 A | 4/1992 |
| JP | 05-163118 A | 6/1993 |
| JP | 08-040832 A | 2/1996 |
| JP | 10-306016 A | 11/1998 |
| JP | 2002-161025 A | 6/2002 |
| JP | 2002-322034 A | 11/2002 |
| JP | 2006-312596 A | 11/2006 |

* cited by examiner

*Primary Examiner* — Michael G Hartley
*Assistant Examiner* — Robert Cabral
(74) *Attorney, Agent, or Firm* — Westerman, Hattori, Daniels & Adrian, LLP

(57) ABSTRACT

The present invention provides a curable resin composition for coating natural or artificial nails, which in particular exhibits an excellent appearance after coating, high water and scratch resistances, and low levels of odor, damage to nails, and dermal irritancy, resulting in a high level of safety to human bodies and superior storage stability. The curable resin composition for coating a natural or artificial nail of the present invention comprises (A) an aqueous emulsion of a polymer having functional groups polymerizable by exposure to active energy radiation, (B) polyethylene glycol, and (C) a photo radical initiator containing no nitrogen atom in its molecule.

18 Claims, No Drawings

CURABLE RESIN COMPOSITION FOR COVERING A FINGERNAIL OR ARTIFICIAL FINGERNAIL

FIELD OF THE INVENTION

The present invention relates to a curable resin composition for coating natural or artificial nails. In particular, the present invention relates to a curable resin composition for coating natural or artificial nails for the purpose of decoration and/or protection.

BACKGROUND ART

Recently, there has been a growing consumer demand for resin materials, such as so-called fingernail polishes, toenail polishes, and sculptures, which are applied to nails to decorate or reinforce the nails for the purposes of decorating natural nails or artificial nails that are glued over natural nails or preventing nails from chipping or peeling due to an external force applied during exercises. The mainstream of toughened keratin coating materials used for decoration or reinforcement is a nitrocellulose based lacquer dissolved in an organic solvent to which pigments having various color tones are added. In addition to this, various keratin coating materials are used, for example, an alkyd resin based lacquer containing pigments and plasticizers. These keratin coating materials provide a coating surface exhibiting excellent gloss in a short time after being applied to the keratin of nails and then the solvent being evaporated. Meanwhile, a coating formed on nails can be readily wiped off with an organic solvent such as acetone.

Such keratin coating materials however inevitably contains organic solvents. A problem of the materials is that the user directly inhales evaporating organic solvents during coating. Furthermore, the formed coating cannot be readily removed with water. It must be wiped off with, for example, a large amount of organic solvent, which has a strong odor and an adverse effect on the user's health. Moreover, organic solvents have a risk of decreasing the physiological function of nails and skin. In addition, most organic solvents are flammable and can be significantly dangerous for household use.

Examples of commonly known keratin coating materials include compositions containing non-reactive polymers and compositions containing reactive curable resins. A solvent or diluent contained in a composition containing a non-reactive polymer is evaporated to form a polymer coating. The formation of the coating, which involves no chemical reaction, has advantages in high stability during storage and low physiological irritancy. Unfortunately, a coating formed on the keratin without chemical cross-links cannot be tough and can be peeled off readily by external forces such as scratching.

Meanwhile, a composition containing a reactive curable resin can form a tough coating composed of a chemically cross-linked polymer. The chemical reaction however must proceed under a relatively moderate condition to minimize the effects on human bodies. Consequently, the reaction of a composition prepared in such manner gradually proceeds during storage, which results in poor preservability. Moreover, such a composition causes a physical irritation more significant than that caused by a non-reactive composition since the chemical reaction proceeds on human bodies.

Patent Literature 1 discloses a photo-crosslinkable nail polish composition containing a polymer having ethylenic double bonds and a predetermined amount of free-radical photo-initiator in a physiologically acceptable medium. Examples of the polymer having ethylenic double bonds include ethylenically unsaturated polyesters, polyesters containing (meth)acrylate side groups and/or end groups, polyurethanes and/or polyureas containing (meth)acrylate groups, polyethers containing (meth)acrylate groups, epoxy acrylates, poly ($C_{1-50}$ alkyl (meth)acrylates) having at least two functional groups containing ethylenic double bonds on the hydrocarbon-based side chains and/or end chains, polyorganosiloxanes containing (meth)acrylate or (meth)acrylamide groups, perfluoropolyethers containing acrylate groups, and dendrimers and hyperbranched polymers containing (meth)acrylate or (meth)acrylamide groups. In addition to these materials, the photo-crosslinkable nail polish composition may include adjuvants and additives commonly used in nail polishes such as pigments or colorants, plasticizers, coalescing agents, preserving agents, waxes, thickeners, fragrances, UV screening agents, cosmetic active agents for nail care, spreading agents, defoaming agents, and dispersants. The technology attempts to solve a toxicity problem of a photo-crosslinkable cosmetic composition by employing reactive components having a sufficiently high molecular mass, instead of highly reactive molecules having a small molecular mass, to prevent them from diffusing towards the neighboring biological substrates. Unfortunately, the toxicity problem is not sufficiently solved and the appearance after curing is not satisfactory.

Patent Literature 2 discloses a solvent-free photocurable nail polish comprising a compound having a polymerizable unsaturated group and a photoinitiator. The compound having a polymerizable unsaturated group refers to a monomer or oligomer having a polymerizable unsaturated group. Examples of the compound include a large number of materials such as polyethylene glycol diacrylate, ethoxy diethylene glycol acrylate, phenoxyethyl acrylate, and phenoxy polyethylene glycol acrylate. In addition to these materials, the solvent-free photocurable nail polish may contain photoinitiating aids, colorants, pearly polishing agents, delustering agents, fragrances, ultraviolet absorbing agents, humectants, defoaming agents, coupling agents, and thixotropic agents. The object of the technology is to provide a solvent-free nail polish. Unfortunately, the polish has a number of adverse effects on human bodies that result from a direct application to human bodies of a compound having a polymerizable unsaturated group, a photoinitiator, and other additives without being diluted due to solvent-free formulation. Another disadvantage of the solvent-free nail polish is nonuniform coating on nails due to its high viscosity.

Patent Literature 3 discloses a nail polish containing a photocurable resin and a coating remover mixed in a nailpolish organic solvent. The photocurable resin used therein is α-hydroxycyclohexyl phenyl ketone and the coating remover is polyester urethane acrylate. In the embodiment of a combination of a base coat agent and a color polish, further used are triethylene glycol dimethacrylate, polyether-modified silicone oil, epoxy methacrylate, and epoxy acrylate. The technology is effective in drying instantly and in being able to peel off without damaging the surface of natural nails. Unfortunately, the polish, which is nonaqueous, does not exhibit sufficient safety to human bodies and thus requires careful attention during handling.

Patent Literature 4 discloses an aqueous nail polish composed of aqueous pigment dispersion and aqueous resin emulsion, the dispersion containing a surfactant and/or an addition polymer of ethylenically unsaturated monomers including an α, β-mono-ethylenically unsaturated acid; and a method of making the polish. The aqueous resin emulsion used therein is, for example, prepared by polymerization of a monomer with a reactive surfactant, the monomer is selected from the group consisting of α, β-ethylenically unsaturated carboxylic acid, methacrylic acid ester, acrylic acid ester, and styrene. Patent Literature 5 discloses an aqueous nail polish containing a resin prepared by polymerization of a monomer with a reactive surfactant, the monomer is selected from the group consisting of α, β-ethylenically unsaturated carboxylic acid, methacrylic acid ester, acrylic acid ester, and styrene. These nail polishes may include, for example, pH regulators, pigments, dyes, dispersing aids, medicaments, ultraviolet absorbing agents, disinfectants, antiseptics, fragrances, plasticizers such as glycolic coating-forming agents, coating-smoothing agents, and thickeners. These nail polishes, which are aqueous, pose no risk such as health impairment or degradation of nails. Moreover, they provide a coating having high adhesion to nails, gloss, and color tone, and the formed coating has high water resistance. Unfortunately, these aqueous nail polishes, which contain non-reactive polymers as mentioned above, have problems of insufficient adhesion to nails and of peeling off readily by an external force such as scratching.

Patent Literature 6 discloses an aqueous nail polish containing at least two different acrylic polymer emulsions having a difference in glass transition temperature therebetween of 10° C. or more. In addition to these materials, the aqueous nail polish may contain, for example, coating-forming aids, plasticizers, pigments, dyes, antiseptics, fragrances, and thickeners. Examples of the coating-forming aids and plasticizers include an extremely large number of materials such as ethylene glycol, propylene glycol, pentaerythritol, glycerol, liquid paraffin, chlorinated paraffin, and machine oil. Compared to aqueous nail polishes containing merely an acrylic polymer emulsion, the aqueous nail polish, which contains at least two different predetermined acrylic polymer emulsions, exhibits somewhat improved gloss, adhesion, and coating hardness. Unfortunately, the endurances such as adhesion, scratch resistance, and toughness of coating are still unsatisfactory.

Patent Literature 7 discloses an aqueous nail polish containing an aqueous emulsion of a self-emulsifiable vinyl polymer and a cellulose derivative. In addition to these materials, the aqueous nail polish may contain, for example, plasticizers, coating-forming aids, pigments, thickeners, dyes, antiseptics, and fragrances. The aqueous nail polish has superior properties such as adhesion, scratch resistance, and water resistance, which leads to excellent gloss and long lastingness. Unfortunately, the water resistance is still unsatisfactory and the polish cannot be used practically due to a drawback of peeling off readily during daily use.

CITATION LIST

Patent Literatures

Patent Literature 1: Japanese Patent Application Laid-Open 2002-322034
Patent Literature 2: Japanese Patent Application Laid-Open 2002-161025
Patent Literature 3: Japanese Patent Application Laid-Open 2006-312596
Patent Literature 4: Japanese Patent Application Laid-Open H8-40832
Patent Literature 5: Japanese Patent Application Laid-Open H5-163118
Patent Literature 6: Japanese Patent Application Laid-Open H4-103513
Patent Literature 7: Japanese Patent Application Laid-Open H10-306016

SUMMARY OF THE INVENTION

Technical Problem

The present invention provides a curable resin composition for coating natural or artificial nails, which in particular exhibits an excellent appearance after coating, high water and scratch resistance, and low levels of odor, damage to nails, and dermal irritancy, resulting in a high level of safety to human bodies and superior storage stability.

Solution to Problems

In order to solve the above problems, the present inventors have extensively studied the techniques described above in various ways and found that solvent-free or nonaqueous compositions as disclosed in Patent Literatures 2 and 3 cannot ensure sufficient safety to human bodies, in particular, nails. Meanwhile, aqueous compositions as disclosed in Patent Literatures 4 and 5 can be highly safe to human bodies. Unfortunately, a composition containing non-reactive polymers cannot provide sufficient adhesion of coating to nails, and the formed coating is readily peeled off by an external force such as scratching. In order to enhance the adhesion of the coating to nails, one possible way is to focus on, for example, the nature of polymers to be used as disclosed in Patent Literatures 6 and 7. Unfortunately, any composition containing non-reactive polymers has a limiting factor of improving its adhesion. As a result, an aqueous composition can avoid the use of organic solvents and can alleviate adverse effects of the contained polymers on human bodies, resulting in formation of a composition with a higher level of safety. A composition further containing a reactive material that can be cured on nails can form a coating having sufficient adhesion to nails. Unfortunately, such an aqueous composition, which contains a material that cures on nails, cannot be sufficiently safe to human bodies. For example, Patent Literature 1 discloses elimination of the use of a reactive monomer having a small molecular weight in order to ensure safety to human bodies. Unfortunately, the elimination is still insufficient to ensure safety to human bodies. The present inventors have further studied on how to enhance the safety of human bodies while sufficient adhesion to nails of the formed coating is kept. As a result, the inventors have found that a component (B), polyethylene glycol, added to predetermined components (A) and (C), not only adjusts the viscosity of the composition, but also penetrate into a network of the component (A)-based resin during formation of a curable coating, resulting in occlusion of slightly remaining unreacted functional groups of the component (A) after the coating is cured. Thereby the unreacted functional groups barely react with nails. In addition, the component (C), which contains no nitrogen atom in its molecule, exhibits less odor and color after being applied to natural or artificial nails and causes, for example, no color change due to aging. Consequently, the present inventors has found that a curable resin composition for coating natural or artificial nails can reduce physiological irritancy and accomplished the present invention that can solve all the above problems. The techniques described above disclose addition of various additives, but does not disclose the addition of polyethylene glycol at all. An aqueous curable resin composition for coating natural or artificial nails which contains materials that cure on human bodies such as nails and further contains polyethylene glycol, exhibits safety to human bodies characteristic in the aqueous composition and superior adhesion to nails characteristic in the reactive material, and can alleviate significant physiological irritancy that is a drawback of the reactive material at the same time. Thereby the composition ensures the safety of human bodies and provides significantly excellent appearance after coating.

Accordingly, the present invention provides:

(1) A curable resin composition for coating a natural or artificial nail comprising (A) an aqueous emulsion of a polymer having functional groups polymerizable by exposure to active energy radiation, (B) polyethylene glycol, and (C) a photo radical initiator containing no nitrogen atom in its molecule.

As preferred Aspects of the present invention, mention may be made of:

(2) The curable resin composition for coating a natural or artificial nail according to Aspect (1), wherein the functional group polymerizable by exposure to active energy radiation is a (meth)acryloyl group;

(3) The curable resin composition for coating a natural or artificial nail according to Aspect (1) or (2), wherein the polymer having functional groups polymerizable by exposure to active energy radiation comprises a polyacrylic backbone or a polyurethane backbone in its main chain structure;

(4) The curable resin composition for coating a natural or artificial nail according to Aspect (1) or (2), wherein the polymer having functional groups polymerizable by exposure to active energy radiation comprises a polyacrylic backbone in its main chain structure;

(5) The curable resin composition for coating a natural or artificial nail according to any one of Aspects (1) to (4), wherein the content of the polymer having functional groups polymerizable by exposure to active energy radiation ranges from 25 to 55% by mass in the aqueous emulsion (A);

(6) The curable resin composition for coating a natural or artificial nail according to any one of Aspects (1) to (5), wherein the polymer having functional groups polymerizable by exposure to active energy radiation has a number average molecular weight ranging from 10,000 to 500,000;

(7) The curable resin composition for coating a natural or artificial nail according to any one of Aspects (1) to (6), wherein the polymer having functional groups polymerizable by exposure to active energy radiation contains at least two functional groups per molecule;

(8) The curable resin composition for coating a natural or artificial nail according to any one of Aspects (1) to (7), wherein the polyethylene glycol (B) is contained in an amount of 0.1 part to 30 parts by mass relative to 100 parts by mass of the polymer having functional groups polymerizable by exposure to active energy radiation in the aqueous emulsion (A);

(9) The curable resin composition for coating a natural or artificial nail according to any one of Aspects (1) to (7), wherein the polyethylene glycol (B) is contained in an amount of 2 parts to 20 parts by mass relative to 100 parts by mass of the polymer having functional groups polymerizable by exposure to active energy radiation in the aqueous emulsion (A);

(10) The curable resin composition for coating a natural or artificial nail according to any one of Aspects (1) to (7), wherein the polyethylene glycol (B) is contained in an amount of 3 parts to 15 parts by mass relative to 100 parts by mass of the polymer having functional groups polymerizable by exposure to active energy radiation in the aqueous emulsion (A);

(11) The curable resin composition for coating a natural or artificial nail according to any one of Aspects (1) to (10), wherein the polyethylene glycol (B) has a weight average molecular weight of 1,000 to 2,000;

(12) The curable resin composition for coating a natural or artificial nail according to any one of Aspects (1) to (11), wherein the photo radical initiator (C) is contained in an amount of 1 part to 10 parts by mass relative to 100 parts by mass of the polymer having functional groups polymerizable by exposure to active energy radiation in the aqueous emulsion (A);

(13) The curable resin composition for coating a natural or artificial nail according to any one of Aspects (1) to (12), wherein the photo radical initiator (C) is ethyl (2,4,6-trimethylbenzoyl)phenylphosphinate, 1-benzoyl-1-cyclohexanol, or a mixture thereof;

(14) The curable resin composition for coating a natural or artificial nail according to any one of Aspects (1) to (13), further comprising (D) wax derived from natural sources;

(15) The curable resin composition for coating a natural or artificial nail according to any one of Aspects (1) to (13), wherein the wax derived from natural sources (D) is contained in an amount of 0.1 part to 15 parts by mass relative to 100 parts by mass of the polymer having functional groups polymerizable by exposure to active energy radiation in the aqueous emulsion (A);

(16) The curable resin composition for coating a natural or artificial nail according to any one of Aspects (1) to (13), wherein the wax derived from natural sources (D) is contained in an amount of 5 parts to 10 parts by mass relative to 100 parts by mass of the polymer having functional groups polymerizable by exposure to active energy radiation in the aqueous emulsion (A); and (17): The curable resin composition for coating a natural or artificial nail according to any one of Aspects (14) to (16), wherein the wax derived from natural sources (D) is at least one selected from the group consisting of carnauba wax, beeswax, palm wax, urushi wax, and insects wax.

Advantageous Effects of the Invention

The curable resin composition for coating a natural or artificial nail of the present invention provides an excellent appearance after coating and exhibits superior properties in water and scratch resistances, resulting in formation of a long-lasting coating without being peeled off after coating. Thereby the coating formed on, for example, nails can have an attractive appearance over the long term and can effectively protect and reinforce nails. In addition, the composition has low levels of odor, damage to nails, and dermal irritancy, resulting in a high level of safety to human bodies. Consequently, the composition requires no label with any hazard marking or risk phrase in accordance with the Globally Harmonized System of Classification and Labeling of Chemicals (GHS). Furthermore, the composition has superior storage stability.

DESCRIPTION OF THE PREFERRED EMBODIMENTS

The polymer contained in the aqueous emulsion of the component (A) can have any functional group polymerizable by exposure to active energy radiation without restriction. Examples of the functional group include various ethylenic double bonds described in Patent Literature 1. Preferred are (meth)acryloyl groups. The polymer has preferably at least two functional groups per molecule. Although any greater number of groups can be contained, a preferred number is five or below. Thereby the polymer can be sufficiently cross-linked after being cured.

Any polymer can be used without restriction as the polymer, which is a backbone, having the above functional groups. Examples of the polymer include polyesters, polyurethanes, polyureas, polyethers, polyorganosiloxanes, and perfluoropolyethers described in Patent Literature 1, as same as the above. In addition, (meth)acrylic resins can also be included. Among them, preferred in the present invention is a polymer having a polyacrylic backbone or a polyurethane backbone in its main chain structure. Particularly preferred is a polymer having a polyacrylic backbone in its main chain structure because such a polymer can reduce damages of nails caused by penetration and can provide a cured material with a uniform hardness.

Examples of the polymer having functional groups polymerizable by exposure to active energy radiation contained in the aqueous emulsion of the component (A) include various polymers forming the above backbones bonded with the above various functional groups, namely, ethylenically unsaturated polyesters, polyesters containing (meth)acrylate side chain groups and/or end groups, polyurethanes and/or polyureas containing (meth)acrylate groups, polyethers containing (meth)acrylate groups obtained by esterifying the hydroxyl end groups of $C_{1-4}$ alkylene glycol homopolymers or copolymers with (meth)acrylic acid, epoxy acrylates, poly ($C_{1-50}$ alkyl (meth)acrylates) having at least two functional groups containing ethylenic double bonds on the hydrocarbon-based side chains and/or end chains, polyorganosiloxanes containing (meth)acrylate or (meth)acrylamide groups, perfluoropolyethers containing acrylate groups, and dendrimers and hyperbranched polymers containing (meth)acrylate or (meth)acrylamide groups. Particularly preferred in the present invention is a polymer having (meth)acryloyl groups polymerizable by exposure to active energy radiation and a polyacrylic backbone in its main chain structure.

In the present invention, the polymer having functional groups polymerizable by exposure to active energy radiation has a number average molecular weight limited up to preferably 500,000, more preferably 300,000. The lower limit is preferably 10,000, more preferably 50,000. A number average molecular weight above the upper limit leads to exceedingly high viscosity, resulting in poor emulsion stability and low workability during coating. Meanwhile, a number average molecular weight below the lower limit leads to insufficient growth of a coating after being cross-linked and cured, resulting in a less flexible coating that cannot sufficiently follow the surface of natural or artificial nails, which precludes formation of a coating that is free from peeling off. Furthermore, it causes higher toxicity due to polymers which cannot be reduced even with the addition of polyethylene glycol of the component (B) to a level that is sufficiently safe to human bodies.

In a preferred embodiment of the present invention, the polymer has (meth)acryloyl groups polymerizable by exposure to active energy radiation and a polyacrylic backbone in its main chain structure, which can be prepared by any known procedures, for example, as follows.

The polymer having a polyacrylic backbone in its main chain structure can be prepared by copolymerization of (meth)acrylic monomer, oligomer, and a small amount of any other required monomers. Preferred examples of the resultant polymer having a polyacrylic backbone in its main chain structure include polymers having reactive groups such as hydroxyl, isocyanate, amino, and carboxyl groups on its end or side chains. (Meth)acryloyl groups are then introduced into the polymer. (Meth)acryloyl groups bonded with urethane can be introduced by a reaction of the polymer having hydroxyl groups with, for example, a compound containing an acrylic group and an isocyanate group such as 2-(meth-acryloyloxy)ethyl isocyanate. Likewise, (meth)acryloyl groups can be introduced by a reaction of the polymer having an amino group with, for example, a compound containing an acrylic group and a carboxy group and the polymer having an isocyanate group with, for example, a compound containing an acrylic group and a hydroxyl group or an amino group. In addition to the above procedure, (meth)acryloyl groups can be directly introduced into the end or side chains of the polymer having a polyacrylic backbone in its main chain structure by living radical polymerization for instance.

Examples of the (meth)acrylic monomer include (meth) acrylic acid alkyl esters such as ethyl acrylate, ethyl methacrylate, methyl acrylate, methyl methacrylate, acrylic acid, methacrylic acid, n-butyl acrylate, n-butyl methacrylate, isopropyl acrylate, isopropyl methacrylate, isobutyl acrylate, isobutyl methacrylate, and 2-ethylhexyl methacrylate; acrylate esters containing hydroxyl groups such as hydroxyethyl acrylate, hydroxyethyl methacrylate, hydroxypropyl acrylate, hydroxypropyl methacrylate, hydroxybutyl acrylate, and hydroxybutyl methacrylate; (meth)acrylamide derivatives such as 2-(1-hydroxyethyl) acrylonitrile, (meth)acrylamide, N-methyl (meth)acrylamide, N,N-dimethyl (meth) acrylamide, and N,N-ethyl (meth)acrylamide; and (meth) acrylic compounds containing glycidyl groups such as glycidyl acrylate and glycidyl methacrylate. These monomers may be replaced with a macromonomer having partly an oligomeric structure. Among them, preferred are ethyl acrylate, methyl methacrylate, acrylic acid, methacrylic acid, n-butyl acrylate, 2-ethylhexyl methacrylate, n-butyl methacrylate, hydroxyethyl acrylate, and hydroxyethyl methacrylate.

Examples of other copolymerizable monomers include styrene, α-methyl styrene, vinyl acetate, vinyl propionate, vinyl chloride, vinylidene chloride, (meth)acrylonitrile, vinyl fluoride, and vinylidene fluoride.

The resultant polymer having functional groups polymerizable by exposure to active energy radiation is emulsified preferably with an alkali. The alkaline treatment is performed while the pH of the aqueous emulsion of the component (A) is maintained at preferably from 6.5 to 9.5, more preferably from 7.0 to 8.0. A pH below the lower limit cannot provide an aqueous emulsion with sufficient dispersibility, whereas a pH above the upper limit causes hydrolysis over time, which may cause chain scission of the polymer. The alkaline treatment can further enhance safety to human bodies and storage stability. Materials preferably used in the alkaline treatment, especially for the polymer having a polyacrylic backbone in its main chain structure, are those reactive with carboxyl groups of the polymer or its esters. Examples of the materials include organic amines such as ammonia, ethylamine, trimethylamine, triethylamine, triisopropylamine, tributylamine, triethanolamine, N-methyldiethanolamine, N-phenyldiethanolamine, monoethanolamine, dimethylethanolamine, diethylethanolamine, morpholine, N-methylmorpholine, and 2-amino-2-ethyl-1-propanol; alkali metals such as lithium, potassium and sodium; and inorganic alkalis such as sodium hydroxide and potassium hydroxide. Among them, preferred in the present invention are alkali metals and inorganic alkalis from the perspective of safety to human bodies. These materials can be used alone or in combination.

In the present invention, the polymer in the aqueous emulsion of the component (A) can be further copolymerized with a monomer having a cross-linkable group. The monomers having a cross-linkable group can be cross-linked therewith and also can be cross-linked with hydroxyl groups on the surfaces of natural or artificial nails and decorated or coated natural or artificial nails after the composition of the present invention is applied to the natural or artificial nails. Thereby internal cross-linkages can steadily proceed even if decorating components having low photocuring ability and pigments or dyes having low light-permeability are used. This can minimize troubles, in particular penetration of a composition into the skin in use. Consequently, the safety to human bodies can be further enhanced. The minimum film forming temperature (MFFT) that is the lowest temperature at which a monomer having a cross-linkable group can be cross-linked, is preferably 25° C. or below, more preferably 10° C. or below. Examples of the monomer having a cross-linkable group to be used include N-methylol(meth)acrylamide, N-methoxymethyl acrylamide, N-butoxymethyl acrylamide, acrylamide and glycidyl (meth)acrylate.

The polymer having functional groups polymerizable by exposure to active energy radiation can be prepared by any known techniques such as emulsion polymerization, bulk polymerization, solution polymerization, suspension polymerization, and precipitation polymerization. From the perspective of the diameter of particles in the resultant aqueous emulsion (A) and its stability, emulsion polymerization is preferable for the preparation of the polymer. Any procedure for the emulsion polymerization can be used without restriction, such as batch polymerization, monomer dropping polymerization, and emulsified-monomer dropping polymerization. In addition, surfactants may be used to further enhance the stability of the aqueous emulsion. The resultant aqueous emulsion (A) contains particles having a diameter in the range of preferably from 5 to 5,000 nm, more preferably from 10 to 1,000 nm. A particle diameter below the lower limit leads to a coating having low water resistance and a composition having low storage stability, whereas a particle diameter above the upper limit causes precipitation of emulsion particles over time, which impairs transparency of a coating and tends to cause white turbidity. From the perspective of safety to human bodies, bulk polymerization can also be preferably used to prepare the aqueous emulsion (A) of the present invention. Particularly preferred is an aqueous emulsion prepared by catalyst-free bulk polymerization.

The aqueous emulsion (A) may contain any amount of water without restrictions that can satisfactory disperse the polymer having functional groups polymerizable by exposure to active energy radiation. The content of the polymer in the aqueous emulsion (A) ranges preferably from 10 to 70% by mass, more preferably from 20 to 60% by mass, still more preferably from 30 to 50% by mass, and particularly preferably from 35 to 45% by mass. A content below the lower limit leads to a coating of the present composition that requires a long time to dry the composition after it is applied to nails, whereas a content above the upper limit cannot satisfactorily disperse the polymer, which may result in precipitation over time.

The component (B), polyethylene glycol, of the present invention may be any known polyethylene glycol prepared by any process. The upper limit of the weight average molecular weight of the polyethylene glycol is preferably 3,000, more preferably 2,000, whereas the lower limit is preferably 500, more preferably 1,000. A molecular weight above the upper limit precludes dissolution and dispersion of the component in a composition, which affects the physical properties of a cured film, namely, a cured film has an excess softness that decreases its scratch resistance. A molecular weight below the lower limit impairs the effect of low physiological irritancy characteristic in polyethylene glycol, and precludes formation of a cured film with flexibility. The content of the component (B), polyethylene glycol, has an upper limit of preferably 30 parts by mass, more preferably 20 parts by mass, and still more preferably 15 parts by mass; and a lower limit of preferably 0.1 part by mass, more preferably 2 parts by mass, and still more preferably 3 parts by mass relative to 100 parts by mass of the polymer having functional groups polymerizable by exposure to active energy radiation. An amount below the lower limit cannot ensure sufficient safety to human bodies, whereas an amount above the upper limit may impairs the stability of an aqueous emulsion.

The photo radical initiator containing no nitrogen atom in its molecule of the component (C) used in the present invention may be any known materials. Examples of the materials include 1-benzoyl-1-cyclohexanol, ethyl (2,4,6-trimethylbenzoyl)phenylphosphinate, benzophenone, 2,2-dimethoxy-2-phenylacetophenone, xanthone, fluorenone, benzaldehyde, fluorene, anthraquinone, 3-methylacetophenone, 4-chlorobenzophenone, 4,4'-dimethoxybenzophenone, benzoin propyl ether, benzoin ethyl ether, benzyl dimethyl ketal, 1-(4-isopropylphenyl)-2-hydroxy-2-methylpropane-1-one, 2-hydroxy-2-methyl-1-phenylpropane-1-one, 1-[4-(2-hydroxyethoxy)-phenyl]-2-hydroxy-2-methyl-1-propane-1-one, thioxanthone, diethyl thioxanthone, 2-isopropyl thioxanthone, 2-chloro thioxanthone, 2-methyl-1-[4-(methylthio)phenyl]-2-morpholino-propane-1-one, and 2,4,6-trimethylbenzoyl diphenylphosphine oxide. Among them, ethyl (2,4,6-trimethylbenzoyl)phenylphosphinate, 1-benzoyl-1-cyclohexanol, and a mixture thereof are preferably used. The photo radical initiator may be commercially available initiators, which include Irgacures 127, 184, 500, 651, 819, 819DW, 907, 1700, 1800, 1870, 2959, and Darocur 1173 (trade marks) available from Ciba Specialty Chemicals K. K.; and Lucirin TPO, TPO-L, and TPO-XO (trade marks) available from BASF SE. Among them, preferred are photo radical initiators that are not classified into any of the categories of environmental hazardousness, toxicity, and irritancy in accordance with the Globally Harmonized System of Classification and Labeling of Chemicals (GHS), for example, Irgacure 184 (1-benzoyl-1-cyclohexanol), Irgacure 2959 (1-[4-(2-hydroxyethoxy)-phenyl]-2-hydroxy-2-methyl-1-propane-1-one), and Lucirin TPO-L (ethyl (2,4,6-trimethylbenzoyl)phenylphosphinate). More preferred are low odor initiators due to for applying to human bodies. Irgacure 184 and TPO-L are preferable since they have particularly low odor. Among them, Irgacure 184 is highly safe and requires no label with any risk phrase in accordance with the GHS. Irgacure 184 is particularly preferred for the reasons that it exhibits low coloration after coating on nails and high absorption of energy radiation that allows curing deep inside a curable film, resulting in formation of a coating having high scratch resistance due to excellent adhesion from the initial stage of the formation of the coating film. In the composition of the present invention, the photo radical initiator of the component (C) contains no nitrogen atom in its molecule. Since the composition of the present invention is for coating natural and artificial nails, preferably the coating film is colorless in appearance and has fewer odors. A photo radical initiator containing a nitrogen atom in its molecule however has some odor and shows high coloration at the initial stage of curing and after the curing. Consequently, such a photo radical initiator is not suitable for the curable resin composition for coating a natural or artificial nail due to unpleasant odor during coating and, for example, discoloration of a coating on nails due to exposure to sunlight over a certain period of time after coating.

The content of the component (C), photo radical initiator, has an upper limit of preferably 10 parts by mass, more preferably 6 parts by mass; and a lower limit of preferably 1 part by mass, more preferably 3 parts by mass relative to 100 parts by mass of the polymer having functional groups polymerizable by exposure to active energy radiation. An amount above the upper limit causes gelation during storage, which leads to a composition having low stability. An amount below the lower limit leads to poor reactivity, which results in a coating that cannot be cured in a short time or with reduced energy.

In addition to the components (A), (B), and (C), the curable resin composition for coating a natural or artificial nail of the present invention may further contain the component (D), wax derived from natural sources, in order to provide a cured film with excellent gloss, resistance to moisture, and thermostability. Examples of the wax derived from natural sources include carnauba wax, beeswax, palm wax, urushi wax, and insects wax. The content of the component (D), wax derived from natural sources, has an upper limit of preferably 15 parts by mass, more preferably 10 parts by mass; and a lower limit of preferably 0.1 part by mass, more preferably 0.5 part by mass relative to 100 parts by mass of the polymer having functional groups polymerizable by exposure to active energy radiation. An amount below the lower limit cannot provide a cured film with excellent gloss, resistance to moisture, and thermostability, whereas an amount above the upper limit reduces the adhesion of a cured film, resulting in significantly low scratch resistance.

The curable resin composition for coating a natural or artificial nail of the present invention may be compounded with any further required materials that do not impair the effect of the present invention, which include viscosity modifiers such as polyurethane, nonionic polyurethane, xanthan gum, hydroxylethyl cellulose, sodium carboxymethyl cellulose, alcohol alkoxylate, sodium polyacrylate, and propylene glycol alginate; leveling agents; defoaming agents (foam breakers); dispersants; substrate wetting agents; synthetic waxes; delustering agents; surfactants; surface controlling agents; aroma chemicals such as fragrances and deodorants; ultraviolet absorbing agents; fillers such as barium sulfate, silicon oxide (fumed silica), talc, and clay; lubricants; pigments (colorants); and polymerization-inhibitors such as hydroquinone and hydroquinone monomethyl ether.

The present invention will now be described in more detail below by way of examples. The present invention, however, should not be limited to these examples.

EXAMPLES

Materials

Materials used in Examples and Comparative Examples are as follows:
<Component (A): Aqueous Emulsion of a Polymer Having Functional Groups Polymerizable by Exposure to Active Energy Radiation>

Aqueous emulsion (1): self-crosslinkable photocuring acrylic emulsion, functional group: acryloyl group, solids content: approximately 40% by mass, number average molecular weight of a polymer: approximately 100,000, CRAYMUL-2717 (trade mark) available from Cray Valley.

Aqueous emulsion (2): non-self-crosslinkable photocuring urethane emulsion, functional group: acryloyl group, solids content: approximately 40% by mass, number average molecular weight of a polymer: approximately 100,000, LUX-2411 (trade mark) available from Alberdingk Boley GmbH.
<Comparative Component (A)>

Acrylate monomer: di(trimethylolpropane) tetraacrylate, Ebecryl 40 (trade mark) available from UCB S. A.

Polyether acrylate: amine modified polyether acrylate, Ebecryl 83 (trade mark) available from UCB S. A.

Urethane acrylate: urethane acrylate oligomer, Craynor 435 (trade mark) available from Cray Valley.
<Component (B): Polyethylene Glycol>

Polyethylene glycol: LIPDXOL 1500 (trade mark) available from Sasol Olefins & Surfactants GmbH, weight average molecular weight: approximately 1,500.
<Comparative Component (B)>

Hydroxyethyl cellulose: METHOCEL K4MSPCG (trade mark) available from The Dow Chemical Company.

Propylene glycol alginate: TEGO COSMO PGA (trade mark) available from Evonik Industries AG.

Sodium carboxymethyl cellulose: Cekol 2000 (trade mark) available from CP Kelco.

Sodium polyacrylate: Cosmedia SP (trade mark) available from Cognis GmbH.

Silica: AEROSIL 200 (trade mark) available from Nippon Aerosil Co., Ltd.
<Component (C): Photo Radical Initiator>

Irgacure 184 (trade mark, available from Ciba Specialty Chemicals K. K., 1-benzoyl-1-cyclohexanol).

Irgacure 500 (trade mark, available from Ciba Specialty Chemicals K. K., mixture of 1-benzoyl-1-cyclohexanol and benzophenone in a mass ratio of 1:1).

Lucirin TPO-L (trade mark, available from BASF SE, ethyl (2,4,6-trimethylbenzoyl)phenylphosphinate).

Benzophenone (available from Wako Pure Chemical Industries, Ltd., reagent).
<Comparative Component (C)>

Irgacure 369 (trade mark, available from Ciba Specialty Chemicals K.K., 2-benzyl-2-dimethylamine-1-(4-morpholino-phenyl)-butanone-1).
<Component (D): Wax Derived from Natural Sources>

Carnauba wax: Carnaubawax (trade mark) available from TOA KASEI CO., LTD.
<Other components>

Leveling and defoaming agents: foam destroying polysiloxane, BYK 028 (trade mark) available from Byk-Chemie GmbH, mixture of foam destroying polysiloxane and hydrophobic solids in polyglycol.
Testing of Material The testings performed in Examples and Comparative Examples are as follows:
<Storage Stability>

Each composition prepared in Examples and Comparative Examples was left at room temperature of 23° C. for 24 hours to evaluate any separation and precipitation which were visually observed. The results of evaluation were indicated with the following symbols:

⊚: No change was observed.

x: Separation and precipitation were observed.
<Water Resistance>

Each composition prepared in Examples and Comparative Examples was applied on fake nails made of polypropylene [SNC nail tips (trade mark) available from SUPER NAIL CENTER] and was then photocured into a cured material. The photocuring was performed for two minutes using an ultraviolet radiation unit at a power rating of 36 watts (four 9-watt lamps). The same procedure was applied to all the following testings. The cured material was then immersed in hot water of 40° C. for eight hours to evaluate any separation and melt of the cured material which were visually observed. The results of evaluation were indicated with the following symbols:

⊚: No change was observed.
x: At least partial separation and precipitation were observed.

<Scratch Resistance>

Each composition prepared in Examples and Comparative Examples was photocured into a cured material as in the testing of water resistance. The surface of the cured material was softly scratched with nails to evaluate any scratch which was visually observed. The results of evaluation were indicated with the following symbols:

⊚: No scratch was observed.
x: A slight scratch was observed.

<Odor>

Each composition prepared in Examples and Comparative Examples was photocured into a cured material as in the testing of water resistance to evaluate any odor which was detected by the human sense of smell before and after curing. The results of evaluation were indicated with the following symbols:

⊚: No or little odor was detected.
○: Slight odor was detected.
Δ: Odor was detected.
x: Significantly strong odor was detected.

<Damages to Nails>

Each composition prepared in Examples and Comparative Examples was applied to a human nail into a size of approximately 1 mm in diameter and then photocured under the same conditions as above. After being left for 30 minutes, the cured material was peeled off from the nail to visually observe the surface of the nail. The results of evaluation were indicated with the following symbols:

⊚: No change was observed on the surface of the nail.
○: The surface of the nail slightly turned white.
x: The surface of the nail turned white.

<Dermal Irritancy>

A single drop of each composition prepared in Examples and Comparative Examples was left on the human skin around nails for one hour. The composition was then washed off with soap and water to evaluate any change in appearance of the skin which was visually observed. The results of evaluation were indicated with the following symbols:

⊚: No change was observed on the appearance of the skin.
x: The skin was at least slightly turned red.

<Appearance Before and After Curing>

Each composition prepared in Examples and Comparative Examples was applied to the human nails to evaluate the surface appearance of the composition before and after the composition was photocured under the same conditions as above. The results of evaluation were indicated with the following symbols. In the case that the composition had appearance that cannot be indicated with these symbols, any change in color was described. In Examples 1 to 12 and Comparative Examples 1 to 6, the evaluation was performed on only the surface appearance of the composition after curing.

⊚: The surface still looked distinctly glossy and reflected fluorescent light on the ceiling clearly.
○: The surface still looked somewhat glossy and reflected fluorescent light on the ceiling.
Δ: The surface looked slightly glossy.
x: No gloss was observed on the coated surface.

<GHS Labeling>

Each composition prepared in Examples and Comparative Examples was evaluated whether any hazard marking is required in accordance with the Globally Harmonized System of Classification and Labeling of Chemicals (GHS). The results of evaluation were indicated with the following symbols:

⊚: No hazard marking was required in the product label.
Xi: Irritancy marking was required.
Xn: Toxicity marking was required.
C: Corrosiveness marking was required.
N: Environmental hazardousness marking was required.

<Risk Phrases>

Each composition prepared in Examples and Comparative Examples was evaluated to fall under which category code number of the classification of toxic chemical materials regulated by the European Union. The category code number refers to a required risk phrase. The results of evaluation were indicated with the following symbols and the category code number refers to as follows:

⊚: No risk phrase was required.
R10: Flammable
R36: Irritating to eyes
R50: Significantly toxic to aquatic organisms
R52: Harmful to aquatic organisms
R53: Possible long-term adverse effects on the aquatic environment
R66: Repeated exposure may cause skin dryness or cracking
R67: Vapors may cause drowsiness and dizziness <Flammability>

Each composition prepared in Examples and Comparative Examples was evaluated for flammability characteristics by a Cleveland open cup flash point test. The results of evaluation were indicated with the following symbols:

⊚: Non-flammable
x: Flammable

Examples 1 to 12 and Comparative Examples 1 to 12

Mixing containers with light-shielded around its periphery were prepared. Each component, in an amount (part by mass) shown in Table 1 or 2, was then put into the corresponding mixing container and thoroughly mixed with stirring at room temperature into a homogeneous composition. The resultant composition was subjected to each of the above testings to evaluate. The results of evaluation are shown in Tables 1 and 2.

TABLE 1

| Component | Composition | Examples |  |  |  |  |  |  |  |  |  |  |  |
|---|---|---|---|---|---|---|---|---|---|---|---|---|---|
|  |  | 1 | 2 | 3 | 4 | 5 | 6 | 7 | 8 | 9 | 10 | 11 | 12 |
| (A) | Aqueous emulsion (1) | 95.0 | 95.0 | 96.5 | 95.0 | 95.0 | 90.0 | 96.0 | 95.5 | 95.5 | — | — | 95.0 |
|  | Aqueous emulsion (2) | — | — | — | — | — | — | — | — | — | 95.0 | 95.0 | — |
| Comparative | Acrylate monomer | — | — | — | — | — | — | — | — | — | — | — | — |
| (A) | Polyether acrylate | — | — | — | — | — | — | — | — | — | — | — | — |
|  | Urethane acrylate | — | — | — | — | — | — | — | — | — | — | — | — |
|  | Purified water | — | — | — | — | — | — | — | — | — | — | — | — |
| (B) | Polyethylene glycol | 2.0 | 2.0 | 0.5 | 2.0 | 2.0 | 7.0 | 2.0 | 2.0 | 2.0 | 2.0 | 2.0 | 2.0 |

TABLE 1-continued

| Component | Composition | 1 | 2 | 3 | 4 | 5 | 6 | 7 | 8 | 9 | 10 | 11 | 12 |
|---|---|---|---|---|---|---|---|---|---|---|---|---|---|
| (C) | Irgacure 184 | 2.0 | 1.5 | 2.0 | 2.0 | 2.0 | 2.0 | 2.0 | — | — | 2.0 | 1.5 | — |
| | Irgacure 500 | — | — | — | — | — | — | — | 1.5 | 1.0 | — | — | — |
| | Lucirin TPO-L | — | 0.5 | — | — | — | — | — | — | 0.5 | — | 0.5 | — |
| | Benzophenone | — | — | — | — | — | — | — | — | — | — | — | 2.0 |
| Comparative (C) | Irgacure 369 | — | — | — | — | — | — | — | — | — | — | — | — |
| (D) | Carnauba wax | 1.0 | 1.0 | 1.0 | 1.0 | 1.0 | 1.0 | — | 1.0 | 1.0 | 1.0 | 1.0 | 1.0 |
| Others | Leveling agents | 0.01 | 0.01 | 0.01 | — | 0.01 | 0.01 | — | 0.01 | 0.01 | 0.01 | 0.01 | 0.01 |
| | Total | 100 | 100 | 100 | 100 | 100 | 100 | 100 | 100 | 100 | 100 | 100 | 100 |
| Results of evaluation | Appearance after curing | ◎ | ◎ | ○ | ○ | ○ | ○ | ○ | ◎ | ◎ | ◎ | ◎ | ◎ |
| | Storage stability | ◎ | ◎ | ◎ | ○ | ◎ | ◎ | ○ | ◎ | ◎ | ◎ | ◎ | ◎ |
| | Water resistance | ◎ | ◎ | ◎ | ◎ | ○ | ○ | ○ | ◎ | ◎ | ◎ | ◎ | ◎ |
| | Scratch resistance | ◎ | ◎ | ○ | ◎ | ◎ | ◎ | ○ | ○ | ○ | ○ | ◎ | ○ |
| | Odor before curing | ○ | ○ | ○ | ○ | ○ | ○ | ○ | ○ | ○ | ○ | ○ | ○ |
| | Odor after curing | ◎ | ◎ | ◎ | ◎ | ◎ | ◎ | ◎ | ◎ | ◎ | ◎ | ◎ | ◎ |
| | Damages to nails | ◎ | ◎ | ◎ | ◎ | ◎ | ◎ | ◎ | ◎ | ◎ | ○ | ○ | ◎ |
| | Dermal irritancy | ◎ | ◎ | ◎ | ◎ | ◎ | ◎ | ◎ | ◎ | ◎ | ◎ | ◎ | ◎ |
| | GHS Labeling | ◎ | ◎ | ◎ | ◎ | ◎ | ◎ | ◎ | ◎ | ◎ | ◎ | ◎ | ◎ |
| | Risk phrases | ◎ | ◎ | ◎ | ◎ | ◎ | ◎ | ◎ | ◎ | ◎ | ◎ | ◎ | ◎ |
| | Flammability | ◎ | ◎ | ◎ | ◎ | ◎ | ◎ | ◎ | ◎ | ◎ | ◎ | ◎ | ◎ |

TABLE 2

| Component | Composition | 1 | 2 | 3 | 4 | 5 | 6 | 7 | 8 | 9 |
|---|---|---|---|---|---|---|---|---|---|---|
| (A) | Aqueous emulsion (1) | — | — | — | — | — | — | — | 95.0 | 97.0 |
| | Aqueous emulsion (2) | — | — | — | — | — | — | — | — | — |
| Comparative (A) | Acrylate monomer | 98.5 | — | — | 98.5 | — | — | — | — | — |
| | Polyether acrylate | — | 98.5 | — | — | 48.5 | — | — | — | — |
| | Urethane acrylate | — | — | 98.5 | — | — | 48.5 | 48.5 | — | — |
| | Purified water | — | — | — | — | 50.0 | 50.0 | 50.0 | — | — |
| (B) | Polyethylene glycol | — | — | — | — | — | — | — | 2.0 | — |
| (C) | Irgacure 184 | — | — | — | 1.5 | — | — | 1.5 | — | 2.0 |
| | Irgacure 500 | 1.5 | 1.5 | 1.5 | — | 1.5 | 1.5 | — | — | — |
| | Lucirin TPO-L | — | — | — | — | — | — | — | — | — |
| | Benzophenone | — | — | — | — | — | — | — | — | — |
| Comparative (C) | Irgacure 369 | — | — | — | — | — | — | — | 2.0 | — |
| (D) | Carnauba wax | — | — | — | — | — | — | — | 1.0 | 1.0 |
| Others | Leveling agents | — | — | — | — | — | — | — | 0.01 | 0.01 |
| | Total | 100 | 100 | 100 | 100 | 100 | 100 | 100 | 100 | 100 |
| Results of evaluation | Appearance after curing | ◎ | ◎ | ◎ | ◎ | ◎ | ◎ | ◎ | Pale yellow | ○ |
| | Storage stability | ◎ | ◎ | ◎ | ◎ | X | X | X | ◎ | ◎ |
| | Water resistance | ◎ | ◎ | ◎ | ◎ | X | X | X | ◎ | ◎ |
| | Scratch resistance | ◎ | ◎ | ◎ | ◎ | ○ | ○ | ○ | ◎ | X |
| | Odor before curing | X | X | X | X | △ | △ | △ | ○ | ○ |
| | Odor after curing | ○ | ○ | ○ | ○ | ○ | ○ | ○ | ◎ | ◎ |
| | Damages to nails | X | X | X | X | X | X | X | ◎ | ◎ |
| | Dermal irritancy | X | X | X | ◎ | X | X | ◎ | ◎ | X |
| | GHS Labeling | ◎ | Xi | ◎ | ◎ | Xi | ◎ | ◎ | N | ◎ |
| | Risk phrases | 52, 53 | 36, 52, 53 | 10, 66, 67 | ◎ | 36, 52, 53 | 10, 66, 67 | ◎ | 50, 53 | ◎ |
| | Flammability | ◎ | ◎ | X | ◎ | ◎ | X | X | ◎ | ◎ |

The component (A) used in Examples 1 to 9 and 12 was aqueous emulsion (1), namely, a polymer having acryloyl groups polymerizable by exposure to active energy radiation and a polyacrylic backbone in its main chain structure. All the examples exhibited satisfactory results. With the component (C), Example 2 using Irgacure 184 and Lucirin TPO-L, Example 8 using Irgacure 500, Example 9 using Irgacure 500 and Lucirin TPO-L, and Example 12 using benzophenone exhibited satisfactory results, like Example 1 using Irgacure 184. The content of the component (B), polyethylene glycol, was varied in Examples 3 and 6. Examples 3 and 6 also exhibited the advantageous effects of the present invention while exhibited somewhat poor appearance after curing, water resistance, scratch resistance, and odor before curing, compared to Example 1. The composition (A) used in Examples 10 and 11 was the aqueous emulsion (2), namely, a polymer having acryloyl groups polymerizable by exposure to active energy radiation and a polyurethane backbone in its main chain structure. These examples exhibited satisfactory results comparable to that in Examples 1 and 2 using the aqueous emulsion (1), namely, a polymer having acryloyl groups polymerizable by exposure to active energy radiation and a polyacrylic backbone in its main chain structure.

In contrast, Comparative Examples 1 to 3 used acrylate monomer, polyether acrylate, and urethane acrylate, respectively, that have been used in known curable resin compositions for coating a natural or artificial nail, without use of the component (B), polyethylene glycol. All of them resulted in high levels of damages to nails and dermal irritancy, and strong odor before curing. Comparative Example 4 differed from Comparative Example 1 in that Irgacure 500 of the component (C) was replaced with Irgacure 184. Similar to Comparative Example 1, Comparative Example 4 resulted in high levels of damages to nails and dermal irritancy, and strong odor before curing. Comparative Examples 5 and 6 used a compound of water with polyether acrylate and urethane acrylate, respectively. The results were significantly poor relative to the cases using aqueous emulsion. Comparative Example 7 differed from Comparative Example 6 in that Irgacure 500 of the component (C) was replaced with Irgacure 184. Similar to Comparative Example 6, the result was significantly poor relative to the cases using aqueous emulsion. Comparative Example 8 used a photo radical initiator containing a nitrogen atom in its molecule instead of the component (C). It resulted in a composition that was matte pale yellow in appearance after curing, which was not usable for the curable resin composition for coating a natural or artificial nail. Comparative Example 9 used no polyethylene glycol of the component (B), which resulted in significantly poor scratch resistance and significantly high dermal irritancy.

Examples 13 to 17 and Comparative Examples 10 to 14

As in prior examples, a basic composition was prepared using each component in an amount (part by mass) shown in Table 3. The base composition was then mixed with the component (B) or the comparative component (B) in an amount (part by mass) shown in Table 4 into a homogeneous composition. The surface appearance of the composition before and after curing was evaluated. The results of evaluation are shown in Table 4.

TABLE 3

| Component | Composition | Base composition |
|---|---|---|
| (A) | Aqueous emulsion (1) | 95.0 |
| (C) | Irgacure 184 | 2.0 |
| (D) | Carnauba wax | 1.0 |
| Others | Leveling agent | 0.01 |
| | Total | 98.01 |

The content of the component (B), polyethylene glycol, was varied in Examples 13 to 17. Although no significant change was observed in appearance after curing, the high content of the component (B) in Example 17 led to a slightly poor appearance before curing, which however did not impair the function of the curable resin composition for coating a natural or artificial nail.

In contrast, Comparative Examples 10 to 14 differed from Example 13 in that hydroxyethyl cellulose, propylene glycol alginate, sodium carboxymethyl cellulose, sodium polyacrylate, and silica, respectively, was used in place of the component (B), polyethylene glycol. All of them resulted in significantly poor appearance before curing, which inhibited these compositions from forming a smooth coating on nails without any asperity on the surface of the coating. Comparative Examples 11 and 12 resulted in poor appearance after curing as well. Comparative Examples 13 and 14 resulted in significantly poor appearance after curing.

INDUSTRIAL APPLICABILITY

The curable resin composition for coating a natural or artificial nail of the present invention provides an excellent appearance after coating and exhibits superior properties in water and scratch resistances, resulting in formation of a long-lasting coating without being peeled off after coating. In addition, the composition has low levels of odor, damage to nails, and dermal irritancy, resulting in a high level of safety to human bodies. Consequently, the composition can be used for decoration and for effectively protecting or reinforcing nails to prevent the nails from chipping for instance. The composition can be used in products of nail care such as fingernail polishes, toenail polishes, and sculptures.

The invention claimed is:
1. A curable resin composition for coating a natural or artificial nail comprising:
   (A) an aqueous emulsion of a polymer having functional groups polymerizable by exposure to active energy radiation;
   (B) polyethylene glycol; and
   (C) a photo radical initiator containing no nitrogen atom in its molecule,
   wherein the polymer having functional groups polymerizable by exposure to active energy radiation is different from the polyethylene glycol (B), and the polymer having functional groups polymerizable by exposure to active energy radiation has a number average molecular weight ranging from 10,000 to 500,000, and polyethyl-

TABLE 4

| | | Examples | | | | | Comparative Examples | | | | |
|---|---|---|---|---|---|---|---|---|---|---|---|
| Component | Composition | 13 | 14 | 15 | 16 | 17 | 10 | 11 | 12 | 13 | 14 |
| | The Base composition | 98.0 | 95.0 | 99.5 | 99.95 | 90.0 | 98.0 | 98.0 | 98.0 | 98.0 | 98.0 |
| (B) | Polyethylene glycol | 2.0 | 5.0 | 0.5 | 0.05 | 10.0 | — | — | — | — | — |
| Comparative | Hydroxyethyl cellulose | — | — | — | — | — | 2.0 | — | — | — | — |
| (B) | Propylene glycol alginate | — | — | — | — | — | — | 2.0 | — | — | — |
| | Sodium carboxymethyl cellulose | — | — | — | — | — | — | — | 2.0 | — | — |
| | Sodium polyacrylate | — | — | — | — | — | — | — | — | 2.0 | — |
| | Silica | — | — | — | — | — | — | — | — | — | 2.0 |
| | Total | 100.0 | 100.0 | 100.0 | 100.0 | 100.0 | 100.0 | 100.0 | 100.0 | 100.0 | 100.0 |
| | Results of evaluation | | | | | | | | | | |
| | Coated appearance before curing | ◎ | ○ | ◎ | ○ | Δ | X | X | X | X | X |
| | Coated appearance after curing | ◎ | ◎ | ○ | ○ | ○ | ○ | Δ | Δ | X | X | ene glycol (B) is contained in an amount of 0.1 part to 30 parts by mass relative to 100 parts by mass of the polymer having functional groups polymerizable by exposure to active energy radiation in the aqueous emulsion (A), wherein the photo radical initiator (C) is ethyl (2,4,6-trimethylbenzoyl)phenylphosphinate 1-benzoyl-1-cyclohexanol or a mixture thereof.

2. The curable resin composition for coating a natural or artificial nail according to claim 1, wherein the functional group polymerizable by exposure to active energy radiation is a (meth)acryloyl group.

3. The curable resin composition for coating a natural or artificial nail according to claim 1, wherein the polymer having functional groups polymerizable by exposure to active energy radiation comprises a polyacrylic backbone or a polyurethane backbone in its main chain structure.

4. The curable resin composition for coating a natural or artificial nail according to claim 1, wherein the polymer having functional groups polymerizable by exposure to active energy radiation comprises a polyacrylic backbone in its main chain structure.

5. The curable resin composition for coating a natural or artificial nail according to claim 1, wherein the content of the polymer having functional groups polymerizable by exposure to active energy radiation ranges from 25 to 55% by mass in the aqueous emulsion (A).

6. The curable resin composition for coating a natural or artificial nail according to claim 1, wherein the polymer having functional groups polymerizable by exposure to active energy radiation contains at least two functional groups per molecule.

7. The curable resin composition for coating a natural or artificial nail according to claim 1, wherein the polyethylene glycol (B) is contained in an amount of 2 parts to 20 parts by mass relative to 100 parts by mass of the polymer having functional groups polymerizable by exposure to active energy radiation in the aqueous emulsion (A).

8. The curable resin composition for coating a natural or artificial nail according to claim 1, wherein the polyethylene glycol (B) is contained in an amount of 3 parts to 15 parts by mass relative to 100 parts by mass of the polymer having functional groups polymerizable by exposure to active energy radiation in the aqueous emulsion (A).

9. The curable resin composition for coating a natural or artificial nail according to claim 1, wherein the polyethylene glycol (B) has a weight average molecular weight of 1,000 to 2,000.

10. The curable resin composition for coating a natural or artificial nail according to claim 1, wherein the photo radical initiator (C) is contained in an amount of 1 part to 10 parts by mass relative to 100 parts by mass of the polymer having functional groups polymerizable by exposure to active energy radiation in the aqueous emulsion (A).

11. The curable resin composition for coating a natural or artificial nail according to claim 1, further comprising (D) wax derived from natural sources.

12. The curable resin composition for coating a natural or artificial nail according to claim 1, wherein a wax derived from natural sources (D) is contained in an amount of 0.1 part to 15 parts by mass relative to 100 parts by mass of the polymer having functional groups polymerizable by exposure to active energy radiation in the aqueous emulsion (A).

13. The curable resin composition for coating a natural or artificial nail according to claim 1, wherein a wax derived from natural sources (D) is contained in an amount of 5 parts to 10 parts by mass relative to 100 parts by mass of the polymer having functional groups polymerizable by exposure to active energy radiation in the aqueous emulsion (A).

14. The curable resin composition for coating a natural or artificial nail according to claim 11, wherein the wax derived from natural sources (D) is at least one selected from the group consisting of carnauba wax, beeswax, palm wax, urushi wax, and insects wax.

15. The curable resin composition for coating a natural or artificial nail according to claim 12, wherein the wax derived from natural sources (D) is at least one selected from the group consisting of carnauba wax, beeswax, palm wax, urushi wax, and insects wax.

16. The curable resin composition for coating a natural or artificial nail according to claim 13, wherein the wax derived from natural sources (D) is at least one selected from the group consisting of carnauba wax, beeswax, palm wax, urushi wax, and insects wax.

17. A process for coating a natural or artificial nail with a curable resin comprising:
(A) an aqueous emulsion of a polymer having functional groups polymerizable by exposure to active energy radiation;
(B) polyethylene glycol; and
(C) a photo radical initiator containing no nitrogen atom in its molecule,
wherein the polymer having functional groups polymerizable by exposure to active energy radiation is different from the polyethylene glycol (B), and the polymer having functional groups polymerizable by exposure to active energy radiation has a number average molecular weight ranging from 10,000 to 500,000, and polyethylene glycol (B) is contained in an amount of 0.1 part to 30 parts by mass relative to 100 parts by mass of the polymer having functional groups polymerizable by exposure to active energy radiation in the aqueous emulsion (A), wherein the photo radical initiator (C) is ethyl (2,4,6-trimethylbenzoyl)phenylphosphinate, 1-benzoyl-1-cyclohexanol, or a mixture thereof.

18. The curable resin composition for coating a natural or artificial nail according to claim 1, wherein the polymer having functional groups polymerizable by exposure to active energy radiation is selected from the group consisting of ethylenically unsaturated polyesters, polyesters containing (meth)acrylate side chain groups and/or end groups, polyurethanes and/or polyureas containing (meth)acrylate groups, polyethers containing (meth)acrylate groups obtained by esterifying the hydroxyl end groups of $C_{1-4}$ alkylene glycol homopolymers or copolymers with (meth)acrylic acid, epoxy acrylates, poly ($C_{1-50}$ alkyl (meth)acrylates) having at least two functional groups containing ethylenic double bonds on the hydrocarbon-based side chains and/or end chains, polyorganosiloxanes containing (meth)acrylate or (meth)acrylamide groups, perfluoropolyethers containing acrylate groups, and dendrimers and hyperbranched polymers containing (meth)acrylate or (meth)acrylamide groups.

* * * * *